(12) United States Patent
Forssmann et al.

(10) Patent No.: US 9,434,780 B2
(45) Date of Patent: Sep. 6, 2016

(54) PROCESS FOR PREPARING HUMAN RELAXIN-2

(75) Inventors: Wolf-Georg Forssmann, Hannover (DE); Thomas Dschietzig, Hannover (DE); Ludger Ständker, Hannover (DE); Andreas Zgraja, Hannover (DE); Jochen Hirsch, Hannover (DE)

(73) Assignee: Relaxera Pharma GmbH & Co. KG i.G., Bensheim (DE)

( * ) Notice: Subject to any disclaimer, the term of this patent is extended or adjusted under 35 U.S.C. 154(b) by 0 days.

(21) Appl. No.: 14/234,919

(22) PCT Filed: Aug. 3, 2012

(86) PCT No.: PCT/EP2012/065218
§ 371 (c)(1),
(2), (4) Date: Apr. 3, 2014

(87) PCT Pub. No.: WO2013/017679
PCT Pub. Date: Feb. 7, 2013

(65) Prior Publication Data
US 2014/0328900 A1    Nov. 6, 2014

(30) Foreign Application Priority Data
Aug. 4, 2011  (DE) .................. 10 2011 109 367

(51) Int. Cl.
C07K 14/64    (2006.01)
(52) U.S. Cl.
CPC ............... *C07K 14/64* (2013.01); *Y02P 20/55* (2015.11)
(58) Field of Classification Search
None
See application file for complete search history.

(56) References Cited

U.S. PATENT DOCUMENTS

| | | | | |
|---|---|---|---|---|
| 5,595,756 A | * | 1/1997 | Bally et al. | 424/450 |
| 2002/0019349 A1 | * | 2/2002 | Conrad et al. | 514/12 |
| 2011/0144019 A1 | * | 6/2011 | Unemori et al. | 514/12.7 |
| 2013/0237481 A1 | * | 9/2013 | Kraynov et al. | 514/12.7 |

FOREIGN PATENT DOCUMENTS

WO    2011042762 A2    4/2011

OTHER PUBLICATIONS

Garber et al (Kidney International, vol. 59 (2001), pp. 876-882).*
Teerlink et al (The Lancet, vol. 373, Issue 9673, Apr. 25-May 1, 2009, pp. 1429-1439).*
Perna et al (Ann N Y Acad Sci. May 2005;1041:431-3).*
Ma (Modern Drug Discovery 2004, 7(6)).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
Barlos et al., An optimized chemical synthesis of human relaxin-2, Journal of Peptide Science, John Wiley and Sons Ltd., GB, 16:200-211 (2010).
Barlos et al., "Synthesis of insulin like peptides. Proposed insulin chain folding mechanism.", Journal of Peptide Science, 18:S29 (2012).
Buellesbach et al., Total Synthesis of Human Relaxin and Human Relaxin Derivatives by Solid-Phase Peptide Synthesis and Site-Directed Chain Combination, Journal of Biological Chemistry, American Society for Biochemistry and Molecular Biology, US, 266:10754-10761 (1991).
Muir et al., "The chemical synthesis of proteins," Current Opinion in Biotechnology, 4:420-427 (1993).
Tang et al., Human gene 2 relaxin chain combination and folding, Biochemistry, American Chemical Society, US, 42:2731-2739 (2003).
Tsetseni et al., Improvements in the chemical synthesis of insulin-like peptides, Advances in Experimental Medicine and Biology, Springer, US, 611:185-186 (2009).
Wade et al., The chemical synthesis of relaxin and related peptides, Annals of the New York Academy of Sciences, 1160:11-15 (2009).
International Search Report and Written Opinion from corresponding PCT Application No. PCT/EP2012/065218 mailed Nov. 14, 2012.

* cited by examiner

*Primary Examiner* — Brian J Gangle
*Assistant Examiner* — Andrea McCollum
(74) *Attorney, Agent, or Firm* — Curtis B. Herbert; Dardi & Herbert, PLLC (57) ABSTRACT

A process for preparing human relaxin-2 having the following amino acid sequence:
A chain:

(SEQ ID NO: 1)
pGlu-Leu-Tyr-Ser-Ala-Leu-Ala-Asn-Lys-Cys-Cys-His-

Val-Gly-Cys-Thr-Lys-Arg-Ser-Leu-Ala-Arg-Phe-Cys

B chain:

(SEQ ID NO: 2)
Asp-Ser-Trp-Met-Glu-Glu-Val-Ile-Lys-Leu-Cys-Gly-

Arg-Glu-Leu-Val-Arg-Ala-Gln-Ile-Ala-Ile-Cys-Gly-

Met-Ser-Thr-Trp-Ser;

comprising the following steps:
providing the amino acids necessary for the synthesis of the A and B chains with usual protective groups, wherein the cysteines are employed as trityl-protected amino acids (L-Cys(Trt)-OH);
effecting a chromatographic purification of the individual chains A and B after the solid state synthesis;
followed by the simultaneous folding and combination of the individual chains A and B in ammonium hydrogencarbonate buffer at pH 7.9 to 8.4; and
subsequent purification of the relaxin-2 formed.

5 Claims, 5 Drawing Sheets

```
                        SEQUENCE LISTING

<160> NUMBER OF SEQ ID NOS: 2

<210> SEQ ID NO 1
<211> LENGTH: 24
<212> TYPE: PRT
<213> ORGANISM: Homo sapiens
<220> FEATURE:
<221> NAME/KEY: DISULFIDE
<222> LOCATION: (11)..(11)
<223> OTHER INFORMATION: Cys-11 of Seq. ID No. 1 with Cys-11 of Seq. ID
      No. 2
<220> FEATURE:
<221> NAME/KEY: DISULFIDE
<222> LOCATION: (24)..(24)
<223> OTHER INFORMATION: Cys-24 of Seq. ID No. 1 with Cys-23 of Seq. ID
      No. 2
<220> FEATURE:
<221> NAME/KEY: DISULFIDE
<222> LOCATION: (10)..(15)
<223> OTHER INFORMATION: Internal disulfide linkage Cys-10 with Cys-15

<400> SEQUENCE: 1

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 2
<211> LENGTH: 29
<212> TYPE: PRT
<213> ORGANISM: Homo sapiens
<220> FEATURE:
<221> NAME/KEY: DISULFIDE
<222> LOCATION: (11)..(11)
<223> OTHER INFORMATION: Cys-11 of Seq. ID No. 2 with Cys-11 of Seq. ID
      No. 1
<220> FEATURE:
<221> NAME/KEY: DISULFIDE
<222> LOCATION: (23)..(23)
<223> OTHER INFORMATION: Cys-23 of Seq. ID No. 2 with Cys-24 of Seq. ID
      No. 1

<400> SEQUENCE: 2

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25
```

PROCESS FOR PREPARING HUMAN RELAXIN-2

CROSS REFERENCE TO RELATED APPLICATIONS

This application is a national phase filing of PCT Application Number PCT/EP2012/065218 filed on Aug. 3, 2012, which claims priority to German Patent Application Number 102011109367.6 filed Aug. 4, 2011, both of which are hereby incorporated herein by reference.

TECHNICAL FIELD

The present patent application relates to a chemical process for the full synthesis of relaxin-2, which is galenically processed into a highly pure form and provided for use as a medicament.

BACKGROUND

Relaxin-2 is a naturally occurring peptide hormone that belongs to the insulin family (Schwabe and McDonald 1977; Rinderknecht and Humbel 1978) and can be isolated from human blood fluid (Wilkinson and Bathgate 2007). However, this would mean an enormous expenditure, not providing the desired and required yields, and in addition, it would be difficult to provide the material in a comparable quality and purity.

SUMMARY OF THE INVENTION

Figure 1:
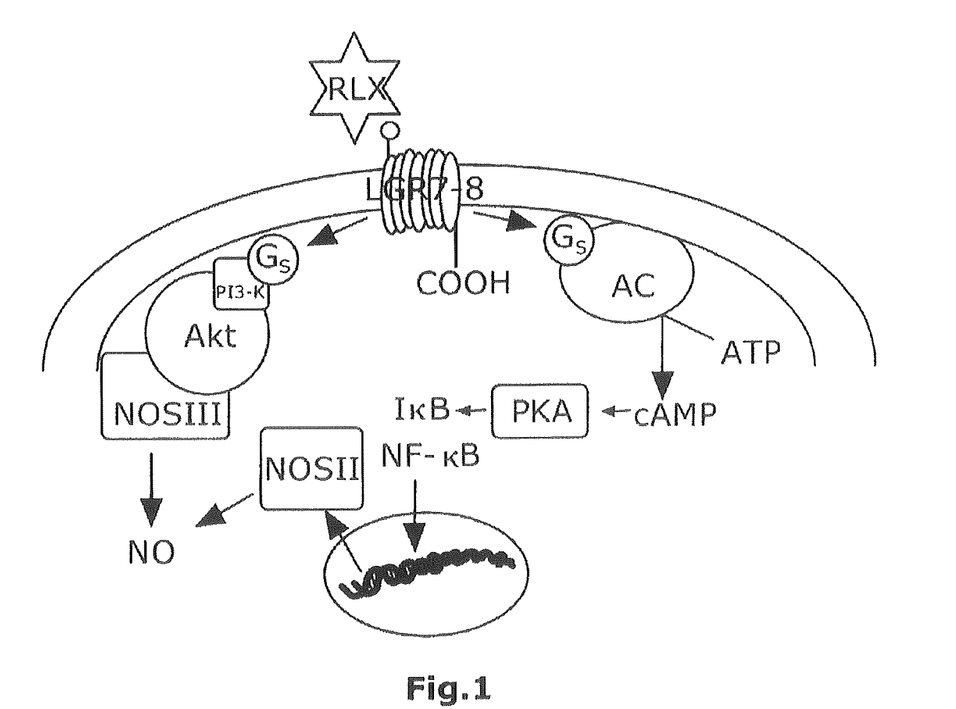
FIG. 1: Representation of relaxin-2 signal transduction: Relaxin-2 (RLX) interacts with the G protein-coupled receptor RXFP1 (LGR7) and can thereby influence the intracellular NO and cAMP concentrations.

The physiological function of relaxin-2 in the human body is to control the cardiovascular and/or renal systems, and the vasodilatory regulation of the vessels (Sherwood 2004). It interacts with a G protein-coupled receptor (see FIG. 1).

Up to the 1990's, relaxin was considered to be exclusively a reproductive and pregnancy hormone: It reaches its highest plasma level in the first trimenon of pregnancy and serves important functions in the implantation of the embryo and the restructuring of the urogenital connective tissue.

Since the year 2000, scientists have dealt with the cardiovascular effects of relaxin, especially its role in chronic heart failure:

The studies have shown for the first time that a constitutively expressed endogenous cardiac and vascular relaxin system exists (Dschietzig et al., 2006). The myocardial relaxin system is in a stimulated state in heart failure; thus, significantly increased circulating relaxin levels are found, which quickly drop when hemodynamics improve.

Thus, the results obtained suggest 1) the existence of a functionally relevant endogenous cardiovascular relaxin system and 2) a compensatory role of relaxin in heart failure.

Like insulin, relaxin-2 consists of two different polypeptide chains (A and B) interconnected by two disulfide bridges (Bourell et al., 1990).

Amino Acid Sequence of Human Processed Relaxin-2
A chain:

(SEQ ID NO: 1)
pGlu-Leu-Tyr-Ser-Ala-Leu-Ala-Asn-Lys-Cys-Cys-His-

Val-Gly-Cys-Thr-Lys-Arg-Ser-Leu-Ala-Arg-Phe-Cys

Molecular Weight of the Linear A Chain: 2656.2 Da (Theoretical)
B chain:

(SEQ ID NO: 2)
Asp-Ser-Trp-Met-Glu-Glu-Val-Ile-Lys-Leu-Cys-Gly-

Arg-Glu-Leu-Val-Arg-Ala-Gln-Ile-Ala-Ile-Cys-Gly-

Met-Ser-Thr-Trp-Ser

Molecular Weight of the Linear B Chain: 3312.9 Da (Theoretical)

Disulfide bridges in the human relaxin-2 molecule:
Within A chain:
Cys-10 with Cys-15
Bridging A chain and B chain:
Cys-11 of A chain with Cys-11 of B chain
Cys-24 of A chain with Cys-23 of B chain
Molecular Weight of the Disulfide-Bridged Molecule:
5963.1 Da (Theoretical)
5962.5 (ESI-MS)

To date, it has been possible to prepare relaxin-2 and other peptides of the relaxin family in sufficient purity only by recombinant synthesis, but this process is tedious for peptides and characterized by low yields (Breece et al., 1995; Tang et al., 2003).

To date, the full chemical synthesis has been associated with a great deal of reaction steps and with a high expenditure and therefore did not give high yields (Bullesbach and Schwabe 1991; Samuel et al., 2007; Barbs et al., 2010).

For the preparation of a medicament, it is necessary to develop an optimized synthetic strategy that meets the demands regarding purity, yield, reproducibility, economic efficiency and expenditure in all cases.

The conventional synthetic strategy is based on the selective introduction of the three disulfide bridges in the relaxin-2 molecule, which means an enormous chemical expenditure on the one hand and requires a chromatographic purification process, which is necessary after each disulfide bridge produced, on the other.

This in turn results in a considerable loss of substance each time in the product to be expected.

In view of the quality and economic aspects of the product, the synthetic strategies that have been performed to date are insufficient.

To date, chemical synthesis has been described to be too difficult to yield products for the market. To date, chemical syntheses have been associated with high impurity levels from the deletion of amino acids, and high costs. Thus, it is desirable to provide a highly pure form of relaxin-2 in order to deal with the constantly increasing challenge to obtain galenic preparations that are free from side effects.

The recombinant synthesis of relaxin-2 was performed by different manufacturers, and the product was provided for preclinical and clinical examinations and studies. However, the expenditure for the production precludes an economically reasonable development.

Numerous studies show that the effect of relaxin is mediated by a G protein-coupled receptor (RXFP1), formerly referred to as orphan receptor LGR7 (Sherwood 2004). In trials with cloned cells carrying the receptor RXFP1, we could detect an effective concentration of peptides in the blood plasma that occur in closed-loop controlled physiological variations and were identified as relaxin. Therefore, a treatment of diseases that are based on deviations from a physiological secretion mode of such factors must involve the provision of a highly pure active ingredient administered in a form adapted to the local targets, which is described in the following and to which the invention relates.

The preparation of relaxin-2 in a highly pure form and its application are difficult and thus must be adapted first to the respective status and object of the treatment. Thus, for certain diseases, galenic forms must be found that allow for systemic and local applications that are adapted to the respective disease. Such formulations for relaxin-2, also in a highly pure form, have not yet been available. Thus, an active ingredient must be available that is sufficiently pure for today's regulations, that can be provided in corresponding galenic forms, that can be produced commercially and that can be considered a highly pure form meeting the highest demands.

An object of the present invention is to provide a process in which relaxin-2 can be prepared in sufficient amounts and with a high efficiency with respect to the educts (A chain+B chain) employed in equimolar amounts for the synthesis, in the subsequent reaction to form the product (relaxin-2).

Another technical problem in need of a solution is the creation of a medicament that provides relaxin in a highly pure form and galenic preparations for a great deal of applications.

According to the invention, these objects are achieved by a process for preparing human relaxin-2 having the following amino acid sequence:

A chain:

```
                                        (SEQ ID NO: 1)
pGlu-Leu-Tyr-Ser-Ala-Leu-Ala-Asn-Lys-Cys-Cys-His-

Val-Gly-Cys-Thr-Lys-Arg-Ser-Leu-Ala-Arg-Phe-Cys
```

B chain:

```
                                        (SEQ ID NO: 2)
Asp-Ser-Trp-Met-Glu-Glu-Val-Ile-Lys-Leu-Cys-Gly-

Arg-Glu-Leu-Val-Arg-Ala-Gln-Ile-Ala-Ile-Cys-Gly-

Met-Ser-Thr-Trp-Ser;
``` wherein the process according to the invention comprises the following steps:
providing the amino acids necessary for the synthesis of the A and B chains with usual protective groups, wherein the cysteines are employed as trityl-protected amino acids (L-Cys(Trt)-OH), effecting a chromatographic purification of the individual chains A and B after the solid state synthesis, followed by the simultaneous folding and combination of the individual chains A and B in ammonium hydrogencarbonate buffer at pH 7.9 to 8.4 and the subsequent purification of the relaxin-2 formed.

In the process according to the invention, the following amino acid derivatives are employed for the solid-state synthesis, in particular:

Fmoc-L-Ala-OH, Fmoc-L-Arg(Pbf)-OH, Fmoc-L-Asn(Trt)-OH, Fmoc-L-Asp(OtBu)-OH, Fmoc-L-Glu(OtBu), Fmoc-L-Cys(Trt), Fmoc-L-Gln(Trt), Fmoc-L-Glu(OtBu)-OH, L-pGlu-OH, Fmoc-Gly-OH, Fmoc-L-His(Trt), Fmoc-L-Ile-OH, Fmoc-L-Leu-OH, Fmoc-L-Lys(Boc)-OH, Fmoc-L-Met-OH, Fmoc-L-Phe-OH, Fmoc-L-Ser(tBu)-OH, Fmoc-L-Thr(tBu)-OH, Fmoc-L-Trp(Boc), Fmoc-L-Tyr(tBu)-OH, and Fmoc-L-Val-OH.

For the synthesis of the B chain, a resin support preloaded with serine as the C-terminal, an Fmoc-protected TentaGel R-PHP, is preferably employed according to the invention. Correspondingly, a resin support preloaded with Fmoc-L-Cys(Trt) as the C-terminal can be employed for the synthesis of the A chain.

The present invention also relates to a medicament containing the human relaxin-2 obtained by the process according to the invention, in addition to usual auxiliary agents and additives. The medicament may contain excipients, such as mannitol, and be in a lyophilized form. For the application, especially for intravenous application, it should be in a form reconstituted in aqueous solutions.

The medicament formulated according to the invention may also be in a form encapsulated in liposomes. The medicament formulated according to the invention may be provided in an applicable form in aqueous solutions containing relaxin-2 encapsulated in liposomes, or be applicable in the form of ointments containing relaxin-2 encapsulated in liposomes.

The present invention also relates to a relaxin-2 obtained by the process according to the invention for the treatment of diseases of the cardiovascular, pulmonary, hepatic and renal systems, including pulmonary hypertension, cardiorenal syndrome, as well as renal and hepatic fibrosis; for the treatment of acute and chronic heart failure including diastolic heart failure and myocardial hypertrophy; for the treatment of diabetes and its consecutive diseases, especially the renal and cardiac damage occurring in diabetes mellitus; for the treatment of proliferative and inflammatory cardiovascular diseases, especially the growth of endothelium and blood vessels, and of the peripheral artery occlusive disease.

The invention is further illustrated by means of the following non-limiting Examples.

DETAILED DESCRIPTION

Example 1

Chemical Synthesis of Highly Pure Relaxin-2

The conventional synthetic strategy is based on the selective introduction of the three disulfide bridges in the relaxin-2 molecule. This means an enormous chemical expenditure on the one hand and requires a chromatographic purification process, which is necessary after each disulfide bridge produced, on the other, which in turn results in a considerable loss of substance in the product to be expected.

In a typical example of an optimized synthesis, relaxin-2 with the amino acid sequence is obtained separately at first in two chains, the A chain and the B chain, wherein a pyroglutamic acid (L-pGlu-OH) is introduced in the N-terminal of the A chain. The original glutamine is modified by ring closure to form a lactam, which blocks Edman sequencing on the one hand and is important to biological activity on the other. Further, the A chain has a cysteine each at positions 10 and 15, which are internally bonded through a disulfide bridge to form cystine. Both cysteines bear a trityl group as an orthogonal acid-labile side chain.

The synthesis of the A chain is preferably effected with Fmoc (9-fluorenyl-methoxycarbonyl) protected amino acids by a stepwise solid phase synthesis and is performed on a Wang resin loaded with F-moc-L-cysteine (0.54 mmol/g, 100-200 mesh) as a solid support (Merrifield et al., 1985). The activation of the Fmoc amino acids, which are employed in a tenfold molar excess, is performed with [(2-(1H-benzotriazol-1-yl)-1,1,3,3-tetramethyluronium hexafluorophosphate] (HBTU, 100 mmol/l) with the addition of 1-hydroxybenzotriazole (HOBt, 0.5 M) and diisopropylethylamine (DIPEA, 2 M) in N-methyl-2-pyrrolidinone (NMP) at room temperature. Acylation reactions are typically performed for 45 minutes. The cleavage of Fmoc is effected with piperidine, 20% in NMP. The synthetic scale of the two chains is 0.1 mM each. The following amino acid derivatives are employed for synthesis: Fmoc-L-Ala-OH, Fmoc-L-Arg(Pbf)-OH, Fmoc-L-Asn(Trt)-OH, Fmoc-L-Asp(OtBu)-OH, Fmoc-L-Glu(OtBu), Fmoc-L-Cys(Trt), Fmoc-L-Gln(Trt), Fmoc-L-Glu(OtBu)-OH, L-pGlu-OH, Fmoc-Gly-OH, Fmoc-L-His(Trt), Fmoc-L-Ile-OH, Fmoc-L-Leu-OH, Fmoc-L-Lys(Boc)-OH, Fmoc-L-Met-OH, Fmoc-L-Phe-OH, Fmoc-L-Ser(tBu)-OH, Fmoc-L-Thr(tBu)-OH, Fmoc-L-Trp(Boc), Fmoc-L-Tyr(tBu)-OH, and Fmoc-L-Val-OH. The synthesis of the B chain corresponds to that of the A chain. However, the resin support employed is one preloaded with serine as the C-terminal, an Fmoc-protected TentaGel R-PHP with 0.19 mmol/g.

For the synthesis of the A chain, a resin support preloaded with cysteine as the C-terminal, an Fmoc-L-Cys(Trt) Wang resin with 0.54 mmol/g, is employed.

Sequence of A chain:

(SEQ ID NO: 1)
pGlu-Leu-Tyr-Ser-Ala-Leu-Ala-Asn-Lys-Cys-Cys-His-

Val-Gly-Cys-Thr-Lys-Arg-Ser-Leu-Ala-Arg-Phe-Cys

MW: 2,656.2 Da

Sequence of B chain:

(SEQ ID NO: 2)
Asp-Ser-Trp-Met-Glu-Glu-Val-Ile-Lys-Leu-Cys-Gly-

Arg-Glu-Leu-Val-Arg-Ala-Gln-Ile-Ala-Ile-Cys-Gly-

Met-Ser-Thr-Trp-Ser

MW: 3,312.9 Da

The synthesis of the two chains is effected exclusively with Fmoc chemistry in a stepwise solid-phase synthesis on an ABI 433 according to the Merrifield principle at room temperature.

Figure 2:
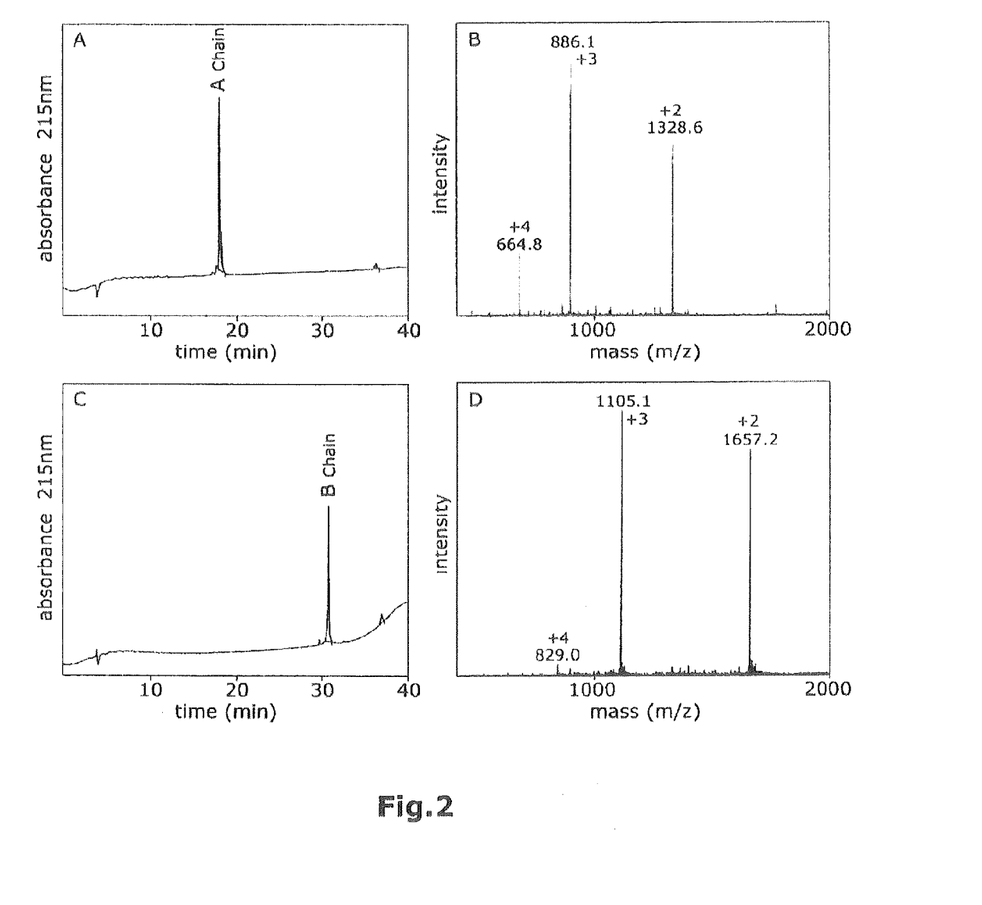
FIG. 2: Analytical HPLC profiles of the precleaned A and B chains (A and C), and the related ESI mass spectra (B and D).

After cleavage of the resin support from the peptidyl resin with trifluoroacetic acid (94% TFA), ethanedithiol (3% EDT) and demineralized water (3%), both chains will have free thiol (SH) groups, as trityl is acid-labile. The raw peptides thus obtained are further purified in a chromatographic step for the following recombination (see FIG. 2).

For combining the A and B chains, these are previously dissolved accordingly in water (A chain) and in 50% acetonitrile (B chain). In order to enable combination of the A chain with the B chain, these are transferred into a buffer system consisting of 2 mM EDTA in 0.1 M $NH_4HCO_3$ solution, pH 7.9-8.4. The buffer system is previously degassed with helium (30 min) to generate an oxygen-free reaction environment.

The dissolved peptide chains are in equimolar concentrations (0.1 mg/ml). For the reaction, it is critical that the addition of cystine and cysteine as a redox pair is effected at a concentration of 2 mg cystine and 2 mg cysteine per mg of peptide employed (A+B chains). The reaction mixture is now stirred moderately at a temperature of 0° C. under a nitrogen blanket for several days.

Figure 3:
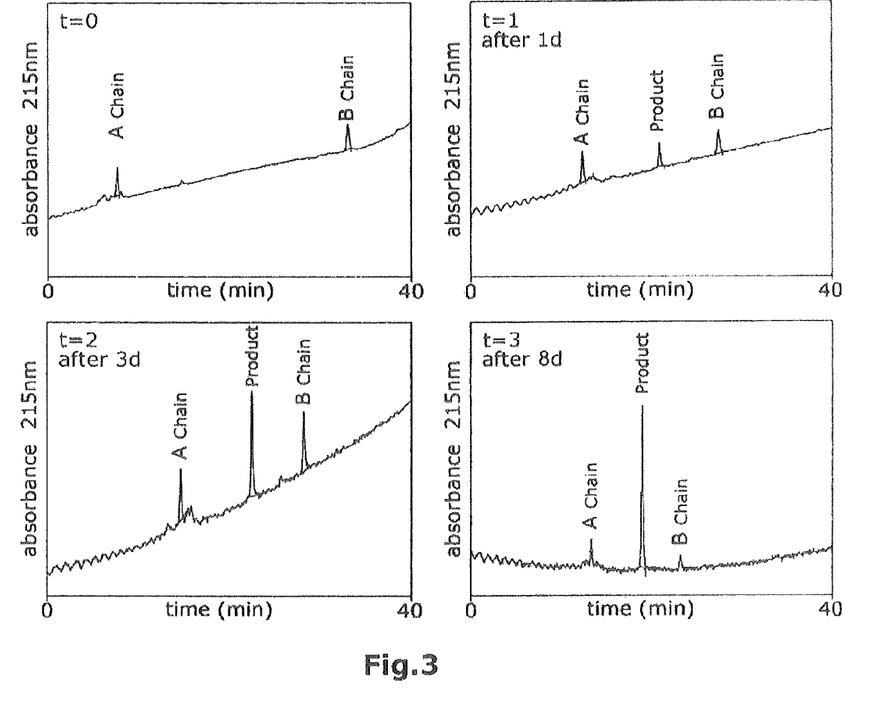
FIG. 3: Reaction kinetics of the two chains to the final product relaxin-2 after 0, 1, 3 and 8 days.

According to experience, the folding reaction can be stopped after several days, and after 9 days at the latest. The reaction in this folding buffer proceeds without possible isomeric structures. The reaction kinetic profiles are logged from t(start) to t(end). The reaction is stopped by means of concentrated TFA at pH 4 (see FIG. 3).

Now, the product obtained is desalted, fractionated and collected by preparative chromatography by means of gradient elution from the reaction mixture. The fractions containing the product are combined and subsequently dried under vacuum (see FIG. 4).

The product is lyophilized for storage and stored at −20° C. The high stability of the preparation of highly pure relaxin-2 in lyophilized form at a temperature of 4° C. has been proven by corresponding analytics, in which fresh material was compared with material stored for several months. After such a storage time, only minor amounts of metabolites appear.

Figure 4:
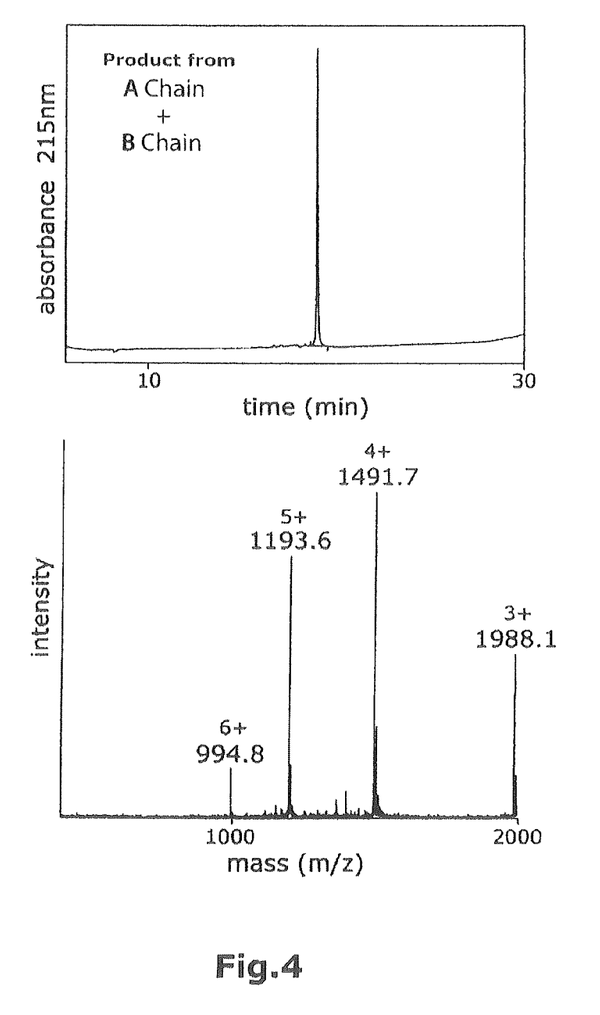
FIG. 4: HPLC profile of the final product relaxin-2 displayed as a plot of absorbance versus time, and the related ESI mass spectrum displayed as a plot of intensity versus mass.
Figure 5:
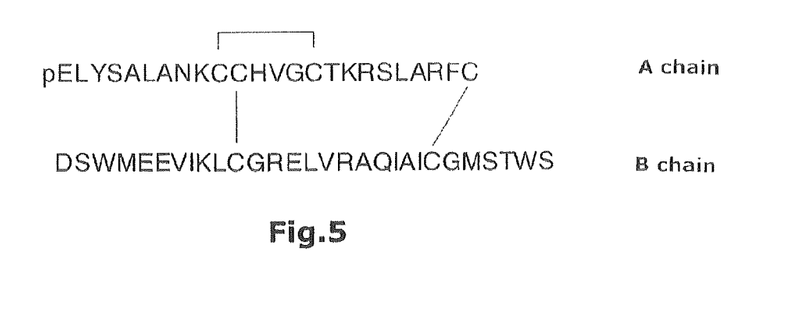
FIG. 5: Disulfide-bridged relaxin-2. Internal bridging of the A chain between Cys-10 and Cys-15. Bridging of A chain with B chain between Cys-11 (A chain) and Cys-11 (B chain), and between Cys-24 (A chain) and Cys-23 (B chain). The measured molecular weight of the final product is 5962.7 Da. A chain has SEQ ID NO:1. B chain has SEQ ID NO:2.

When the A and B chains are combined and 40 mg each is employed, 16-24 mg of the product relaxin-2 having a purity of >98% is obtained (see FIG. 4, 5). This corresponds to a yield of 20-30% after the folding and purification steps.

Example 2

Preparation of the New Formulations of Relaxin-2

Preferably suitable for a galenic application are (i) sterile aqueous solutions, (ii) active ingredient encapsulated in liposomes that may also be applied in a physiological solution, and (iii) active ingredient encapsulated in liposomes that has been processed into an ointment.

After numerous experiments with, for example, polyglycolate/lactate release particles, PEGylation, micropumps etc., it has been surprisingly found that two forms of galenics can be preferably applied:
1. Lyophilized relaxin-2 reconstituted in mannitol;
2. Encapsulation in liposomes (preferably, but not exclusively, ROVISOME®), which is a particularly suitable form, because the active ingredient is very stable except for a few metabolites. Such metabolites also occur as natural forms in blood plasma, but can be avoided by working in a nitrogen atmosphere, and, being natural endogenous derivatives, are free from side effects.

(1) Aqueous Solutions:

According to the inventive application of highly pure active ingredient, a use in aqueous physiological solutions is indicated if short pulsed hormone surges are to be achieved. A preferably suitable formulation of the active ingredient for this purpose is in individual ampoules for intravenous or preferably subcutaneous injection. The highly pure product is first prepared in ampoules or in cartridges for pen injection as a lyophilized active ingredient with an excipient, preferably mannitol, to ensure long-term stability. A therapeutic unit freeze-dried in 10 ml ampoules (or cartridge) stabilized with 20 mg mannitol and acetate as a salt is recommended, whereby storage at refrigerator temperature for more than one year is enabled, and very highly tolerable ingredients are included. For using the formulation, the lyophilizate is brought into a physiologically tolerable solution immediately before injection, for example, by using 0.9% saline.

(2) Liposomal Preparation:

Various liposome preparations differing in the encapsulation efficiency of relaxin-2 were selected. The two most stable formulations are suitable for later use in treatment for subcutaneous injection and as an ointment form.

| | |
|---|---|
| 5.00% | lecithin with a phosphatidylcholine content of >70% |
| 1.67% | isopropanol |
| 1.00% | polysorbate 20 |
| 0.01% | benzalkonium chloride |
| 0.10% | EDTA |
| 0.50% | relaxin-2 |
| Particle size: | about 150 nm |
| pH: | 5.6 |

The liposome preparations are physically stable over a period of >1 month. What results therefrom are stable liposome preparations with an optimum storage temperature at RT (constant particle size; no change in pH and smell).

All raw materials employed meet pharmaceutical specifications, and lecithin has been approved by the U.S. Food and Drug Administration (FDA).

For using the i.v. or s.c. formulation, the liposome preparation is preferably diluted in a physiologically tolerable solution, for example, in 0.9% saline, immediately before injection.

Example 3

Tolerability and Safety of the Relaxin-2 Formulations

The lyophilized form was tested intravenously, the liposomal formulation was tested s.c. directly in aqueous solution, and the base cream was tested, each with a high dose of relaxin-2: a high dose that is above tenfold the expected concentration in clinical application did not show any significant side effects, and in a tolerance test for skin tolerability in rats, no deleterious side effect was found either.

Example 4

Effect on Cell Models (Bioassays)

Studies on cell models have shown that the use of highly pure relaxin exhibits an excellent effect, comparable to that of the recombinant peptide.

The amino acid sequence of the synthetic human relaxin-2 is identical with that of the naturally occurring peptide.

In human embryonic kidney cells (HEK-293T) expressing the natural receptor RXFP1, synthetic hRlx-2 displaces europium-labeled relaxin-2 with the same potency as recombinant human relaxin-2, which demonstrates intact receptor activity.

Figure 6:
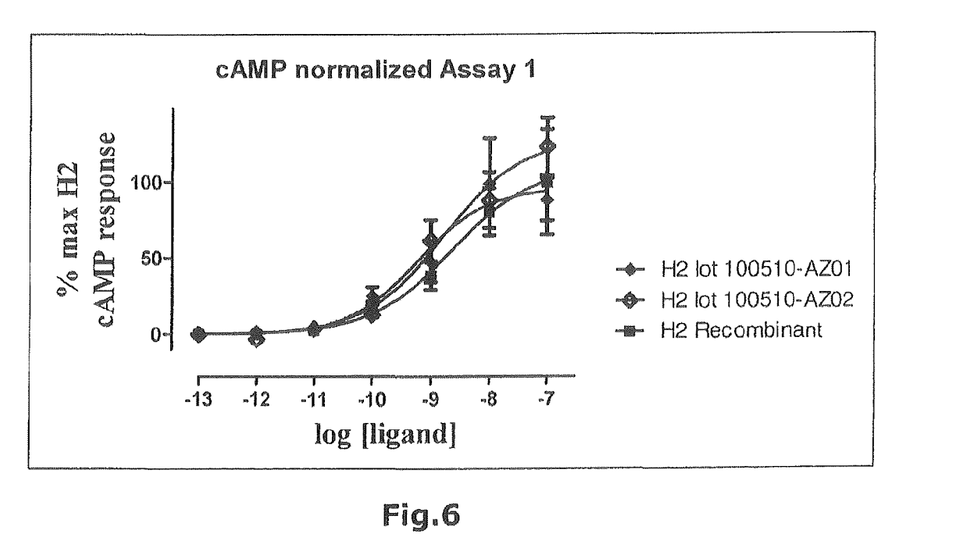
FIG. 6: In a cAMP assay, the batches of relaxin-2 prepared by chemical synthesis (AZ01 and AZ02) have an activity comparable to that of the recombinantly prepared relaxin-2.

In cAMP assays specifically developed for relaxin-2 (Halls et al., 2009) and performed by us in human THP-1 cells, synthetic and recombinant human relaxin-2 showed equivalent bioactivities (see FIG. 6).

In an established cell model of myocardial hypertrophy, synthetic human relaxin-2 is as potent as recombinant human relaxin-2. In this model, relaxin inhibits the differentiation of cardiac fibroblasts into myofibroblasts and the secretion of growth factors by these cells (Dschietzig et al., 2006).

Based on experimental results in animal models (Teichman et al., 2009; Samuel et al., 2006; Schondorf et al., 2007), it is to be recommended that synthetic human relaxin-2 for human therapy should be preferably used for:
  congestive heart failure (with reduced systolic function): acute and chronic treatment
  acute heart failure
  cardiorenal symptoms
  myocardial fibrosis/hypertrophy and diastolic heart failure (with preserved systolic function)
  pulmonary hypertension
  pulmonary, renal or hepatic fibrosis
  peripheral artery occlusive disease
  diabetes mellitus Acute dosage (estimation from a pilot study in human congestive heart failure): 30 to 100 µg/kg/day s.c. (dose of 2.1 to 7.0 mg/day for 70 kg body weight) over 24 to 48 hours.

Chronic dosage (estimation): 10 to 30 µg/kg/day s.c. (0.7 to 2.1 mg/day for 70 kg body weight) over several months.

REFERENCES

Barlos K K, Gatos D, Vasileiou Z, Barlos K. An optimized chemical synthesis of human relaxin-2. J Pept Sci. 2010 April; 16(4): 200-11.

Bourell J H, Canova-Davis E, Ling V T, Laramee G R, Winslow J W, Griffin P R, Rinderknecht E, Vandlen R L. Structural characterization by mass spectrometry of native and recombinant human relaxin. *Biomed. Environ. Mass Spectrom.* 1990; 19: 655-664.

Breece T, Hayenga K, Rinderknecht E, Vandlen R, Yansura D. Process for producing relaxin. WO 1995/000645.

Bullesbach E E, Schwabe C. Total synthesis of human relaxin and human relaxin derivatives by solid-phase peptide synthesis and site-directed chain combination. *J. Biol. Chem.* 1991; 266: 10754-10761.

Dschietzig T, Bartsch C, Baumann G, Stangl K. Relaxin—a pleiotropic hormone and its emerging role for experimental and clinical therapeutics. *Pharmacol. Ther.* 2006; 112: 38-56.

Halls M L, Hewitson T D, Moore X L, Du X J, Bathgate R A, Summers R J. Relaxin activates multiple cAMP signaling pathway profiles in different target cells. Ann N Y Acad Sci. 2009 April; 1160: 108-11.

Merrifield R B. Solid phase synthesis (Nobel Lecture). *Angew. Chem.* 1985; 97: 801-812; *Angew. Chem. Int. Ed.* 1985; 24: 799-810.

Rinderknecht E, Humbel R E. The amino acid sequence of human insulin-like growth factor I and its structural homology with proinsulin. *J. Biol. Chem.* 1978; 253: 2769-2776.

Samuel C S, Du X J, Bathgate R A, Summers R J. 'Relaxin' the stiffened heart and arteries: The therapeutic potential for relaxin in the treatment of cardiovascular disease. *Pharmacol. Ther.* 2006; 112: 529-552.

Samuel C S, Lin F, Hossain M, Zhao C, Ferraro T, Bathgate R A, Tregear G W, Wade J D. Improved chemical synthesis and demonstration of the relaxin receptor binding affinity and biological activity of mouse relaxin. *Biochemistry* 2007; 46: 5374-5381.

Schondorf T, Lubben G, Hoopmann M, Borchert M, Forst T, Hohberg C, Lobig M, Armbruster F P, Roth W, Grabellus M, Pfutzner A. Relaxin expression correlates significantly with serum fibrinogen variation in response to antidiabetic treatment in women with type 2 diabetes mellitus. *Gynecol. Endocrinol.* 2007; 23: 356-360.

Schwabe C, McDonald J K. Relaxin: a disulfide homolog of insulin. *Science* 1977; 197: 914-915.

Sherwood O D. Relaxin's physiological roles and other diverse actions. *Endocr. Rev.* 2004; 25: 205-234.

Tang J G, Wang Z H, Tregear G W, Wade J D. Human gene 2 relaxin chain combination and folding. *Biochemistry* 2003; 42: 2731-2739.

Teichman S L, Unemori E, Dschietzig T, Conrad K, Voors A A, Teerlink J R, Felker G M, Metra M, Cotter G. Relaxin, a pleiotropic vasodilator for the treatment of heart failure. *Heart Fail. Rev.* 2009; 14: 321-329.

Wilkinson T N, Bathgate R A. The evolution of the relaxin peptide family and their receptors. *Adv. Exp. Med. Biol.* 2007; 612: 1-13.

The invention claimed is:

1. A method of treating a disease comprising synthesizing Relaxin-2 and administering the Relaxin-2 for the treatment of pulmonary hypertension, rental fibrosis, or acute heart failure, with the relaxin-2 having the following amino acid sequence: an A chain having SEQ ID NO:1 wherein the first residue Glu is a pyroglutamic acid and a B chain having SEQ ID NO:2, with the synthesizing comprising the following steps:

providing the amino acids necessary for the synthesis of the A and B chains with protective groups, wherein the cysteines are employed as trityl-protected amino acids (L-Cys(Trt)-OH); effecting a solid state synthesis of the individual chains A and B;

effecting a chromatographic purification of the individual chains A and B after the solid state synthesis;

followed by the simultaneous folding and combination of the individual chains A and B in ammonium hydrogencarbonate buffer at pH 7.9 to 8.4;

addition of cystine and cysteine as a redox pair at a concentration of 2 mg cystine and 2 mg cysteine per mg of peptide employed (A+B chains) and subsequent purification of the relaxin-2 formed.

2. The method of claim 1 with the Relaxin-2 being in a lyophilized form with an excipient.

3. The method of claim 2 with the Relaxin-2 being reconstituted in aqueous solution.

4. The method of claim 1 with the Relaxin-2 being encapsulated in liposomes.

5. The method of claim 4 with the Relaxin-2 being in an aqueous solution containing relaxin-2 encapsulated in liposomes, or in an ointment containing relaxin-2 encapsulated in liposomes.

* * * * *

UNITED STATES PATENT AND TRADEMARK OFFICE
CERTIFICATE OF CORRECTION

PATENT NO. : 9,434,780 B2
APPLICATION NO. : 14/234919
DATED : September 6, 2016
INVENTOR(S) : Wolf-Georg Forssmann et al.

It is certified that error appears in the above-identified patent and that said Letters Patent is hereby corrected as shown below:

On the Title Page

Other Publications, Column 2, Lines 14-15, please delete "American Society for Biochemistry and Molecular Biology".

In the Claims

Column 11, Claim 1, Line 3, please delete "rental" and insert --renal--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*